United States Patent [19]
Flippin et al.

[11] Patent Number: 5,753,663
[45] Date of Patent: May 19, 1998

[54] PYRIMIDINE DERIVATIVES

[75] Inventors: Lee Allen Flippin, Woodside; Gabriel Stone Weatherhead, Mountain View, both of Calif.

[73] Assignee: Syntex (U.S.A.) Inc., Palo Alto, Calif.

[21] Appl. No.: 719,062

[22] Filed: Sep. 24, 1996

Related U.S. Application Data

[60] Provisional application No. 60/004,733, Oct. 2, 1995.

[51] Int. Cl.$^6$ .................. C07D 239/00; C07D 239/74; A61K 31/52; A61K 31/505
[52] U.S. Cl. .................. 514/257; 514/267; 544/249; 544/301; 544/245
[58] Field of Search .................. 544/249, 301; 514/257, 267

[56] References Cited

U.S. PATENT DOCUMENTS

| | | | |
|---|---|---|---|
| 3,177,216 | 4/1965 | Wagner | 260/251 |
| 3,257,400 | 6/1966 | Wagner et al. | 260/256.4 |
| 3,925,384 | 12/1975 | Krapcho et al. | 260/256.4 Q |

FOREIGN PATENT DOCUMENTS

WO 93/08176  4/1993  WIPO.

OTHER PUBLICATIONS

Taylor, et al., "Heterocyclic Syntheses from o-aminonitriles-XXVIII", *Tetrahedron*, vol. 23, No. 5, 1967, pp. 2081-2093.
Bennett, "Organolithium Addition to 5,6-Disubstituted Pyrimidines", *J. Heterocycl. Chem.*, vol. 15, No. 4, 1978, pp. 671-674.
Bennett, et al., "Synthesis and Antiinflammatory Activity of Trisubstituted Pyrimidines and Triazines", *J. Med. Chem.*, vol. 221, No. 7, 1978, pp. 623-628.
Hirota, et al., "Polycyclic N-Hetero Compounds. XXIII.", *Chem. Pharm. Bull.*, vol. 34, No. 7, 1986, 3011-3014.
Hirota, et al., "Polycyclic N-Hetero Compounds. XXIX.", *J. Heterocycl. Chem.*, vol. 24. No. 2, 1987, pp. 341-344.
Hirota, et al., "Polycyclic N-Hetero Compounds. XX.", *J. Heterocycl. Chem.*, vol. 23, No. 3, 1986, pp. 685-688.
Hirota, et al., "Polycyclic N-Hetero Compounds. XXXVI.", *J. Heterocycl. Chem.*, vol. 28, No. 2, 1991, pp. 257-261.
Hirota, et al., "Polycyclic N-Hetero Compounds. XXX.", *J. Heterocycl. Chem.*, vol. 26, No. 12, 1987, pp. 3211-3220.
Hirota, et al., "Polycyclic N-Hetero Compounds. XXV.", *J. Heterocycl. Chem.*, vol. 24, No. 4, 1986, pp. 1119-1130.
Deli, Jozsef et al., *Acta Chim. Hung.* (1984), vol. 117, No. 3, pp. 293-305, "Synthesis of 2-Am 4-Aryl-5, 6-Dihydrobenzo[h]Quinazolines and their Derivatives."
Bannet et al., Chem. Abstr. 89:36588, J. Med. Chem. (1978), 21(7), 623-8, 1978.
Chauhan et al., Chem. Abstr. 86:29749, Tetrahedron (1976), 32(14), 1779-87, 1976.
Taylor et al., Chem. Abstr. 67:3061, Tetrahedron (1967), 23(5), 2081-93, 1967.

*Primary Examiner*—Mukund J. Shah
*Assistant Examiner*—Sabiha N. Qazi
*Attorney, Agent, or Firm*—Brian Lewis; Janet K. Kaku

[57] ABSTRACT

The disclosed pyrimidine derivatives, and pharmaceutically acceptable salts thereof, exhibit useful pharmacological properties, in particular use as $5HT_{2C}$- antagonists. The invention is also directed to formulations and methods for treatment.

19 Claims, No Drawings

PYRIMIDINE DERIVATIVES

CROSS REFERENCE TO RELATED APPLICATION

This application claims the benefit under 35 U.S.C. 119(e) of U.S. Provisional Application No. 60/004,733 filed Oct. 2, 1995.

1. Field of the Invention

The present invention relates to novel pyrimidine derivatives, and pharmaceutically acceptable salts thereof, which exhibit useful pharmacological properties, including use as $5HT_{2C}$-antagonists. The invention is also directed to formulations and methods for treatment.

2. Background Information and Related Disclosures

Serotonin, a neurotransmitter with mixed and complex pharmacological characteristics, was first discovered in 1948, and subsequently has been the subject of substantial research. Serotonin, also referred to as 5-hydroxytryptamine (5-HT), acts both centrally and peripherally on discrete 5-HT receptors. The 5-HT receptor is presently delineated into four major subclassifications: $5-HT_1$, $5-HT_2$, $5-HT_3$ and $5-HT_4$ receptors, and subtypes thereof. The $5-HT_1$, and $5-HT_2$ subtypes are also heterogeneous.

The $5-HT_{2C}$ receptor, first characterized as a $5-HT_{1C}$ subtype (see Pazos et al. (1984), *Eur. J. Pharmacol.*, 106, 539–546) and subsequently recognized as belonging to the $5-HT_2$ receptor family (see Pritchett et al. (1988), *EMBO J.*, 7, 4135–4140), is widely distributed in the human brain (see Pazos et al. (1987), *Neuroscience*, 21, 97–122). Current evidence strongly supports a therapeutic role for $5-HT_{2C}$ receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism (see Kennett (1993), *Curr. Opin. Invest. Drugs*, 2, 317–362). Support for these therapeutic indications rests in the clinical and experimental pharmacology reported for 1-(3-chlorophenyl)piperazine, a $5-HT_{2C}$ receptor agonist, non-selective $5-HT_{2C/2A}$ receptor antagonists and selective $5-HT_{2A}$ receptor antagonists (see Kennett (1993), supra.; and Kennett et al. (1994). *Br. J. Pharmacol.*, 111, 797–802). Additional support for the disclosed therapeutic indications for $5-HT_{2C}$ antagonists is seen in that 5-HT reuptake inhibitors, the current therapy of choice for obsessive compulsive disorder, alcoholism and depression (and also becoming more widely accepted for treating panic disorder and migraine) exert their therapeutic efficacy after chronic administration and subsequent alteration (desensitization) of the $5-HT_{2C}$ receptor. Thus, selective $5-HT_{2C}$ receptor antagonists will offer distinct therapeutic advantages collectively in efficacy, rapidity of onset and absence of side effects (see Kennett (1993), supra.).

The disclosures of these and other documents referred to throughout this application (e.g., in the Pharmacology section of the Detailed Description of the Invention) are incorporated herein by reference.

SUMMARY OF THE INVENTION

One aspect of the invention concerns compounds represented by Formula I:

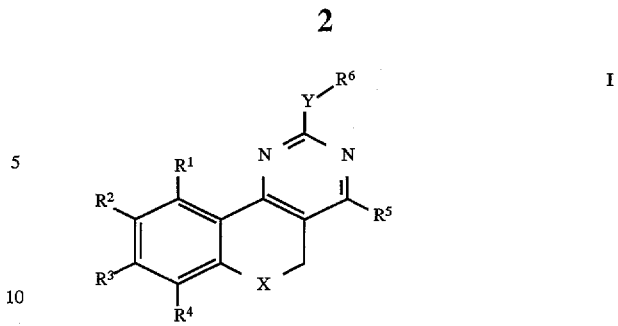

wherein:

$R^1$, $R^2$, $R^3$, $R^4$, and $R^5$ are independently hydrogen, lower alkyl, lower alkoxy, halo, or trifluoromethyl;

X is oxygen, sulfur, $NR^7$, or $CH_2$;

Y is oxygen, sulfur, $NR^7$, or $(CH_2)_n$;

in which n is 0, 1, or 2; and $R^7$ is hydrogen or lower alkyl; and $R^6$ is lower alkyl or optionally substituted aryl; and the pharmaceutically acceptable acid addition salts thereof.

In another aspect, the invention relates to pharmaceutical compositions containing a therapeutically effective amount of a compound of Formula I, or a pharmaceutically acceptable salt thereof, in admixture with one or more pharmaceutically acceptable, non-toxic carriers.

In yet another aspect, the invention relates to a method for treating a mammal having a disease state which is alleviable by treatment with a $5HT_{2C}$ antagonist, by administering to a mammal in need thereof a therapeutically effective amount of a compound of Formula I, or a pharmaceutically acceptable salt thereof.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O— (lower alkyl) wherein lower alkyl is as herein defined.

"Halo" denotes fluoro, chloro, bromo, or iodo, unless otherwise indicated.

The term "aryl" means a monocyclic or bicyclic aromatic ring, and includes carbocycles and heterocycles. Examples of aryl groups include phenyl, naphthyl, thiophene, furan, imidazole, pyridine, pyrimidine, and indole. The aryl group may be attached to the linking group "Y" at any position of the aromatic ring.

"Optional" or "optionally" means that the subsequently described event or circumstance may or may not occur, and that the description includes instances where said event or circumstance occurs and instances in which it does not. For example, "optionally substituted aryl" means that aryl as defined above may or may not be substituted with a substituent selected from the group consisting of lower alkyl, lower alkoxy, hydroxy, nitro, trifluoromethyl and halo, and encompasses unsubstituted aryl groups and all possible isomeric aryl radicals that are mono, di or trisubstituted.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "therapeutically effective amount" refers to that amount of a compound of Formula I that is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

The term "disease state which is alleviable by treatment with a 5HT$_{2C}$ antagonist" as used herein is intended to cover all disease states which are generally acknowledged in the art to be usefully treated with compounds having affinity for 5HT$_{2C}$ receptors in general, and those disease states which have been found to be usefully treated by the specific compounds of our invention, the compounds of Formula I. Such disease states include, but are not limited to, anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism.

The compounds of Formula I, illustrated below, will be named using the indicated numbering system:

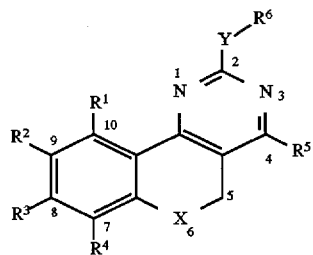

A compound of Formula I wherein $R^1$, $R^2$, $R^3$, and $R^5$ are hydrogen, $R^4$ is methoxy, X is CH$_2$, Y is NH, and $R^6$ is 3,4,5-trimethoxyphenyl is named:

7-methoxy-2-(3,4,5-trimethoxyanilino)-5,6-dihydrobenzo-[h]quinazoline.

Preferred Embodiments

Among the family of compounds of the present invention, one preferred category includes the compounds of Formula I in which X is CH$_2$. Within this category a preferred group includes the compounds where $R^5$ is hydrogen and $R^6$ is optionally substituted aryl. Within this group a preferred subgroup includes those compounds where Y is —NR$^7$, particularly where $R^7$ is hydrogen. Within this subgroup it is preferred that $R^1$, $R^2$, $R^3$, and $R^4$ are lower alkoxy, especially where $R^4$ is methoxy and $R^1$, $R^2$, and $R^3$ are hydrogen. More preferred are those compounds where $R^6$ is phenyl, mono-, di, or trisubstituted by lower alkoxy, especially methoxy and ethoxy, or where $R^6$ is optionally substituted indole, particularly N-methyl substituted.

METHODS OF PREPARATION

Preparation of Compounds of Formula I

One method of preparing compounds of Formula I is shown in Reaction Scheme I below. This method is preferred for the preparation of compounds of Formula I where Y is nitrogen.

REACTION SCHEME I

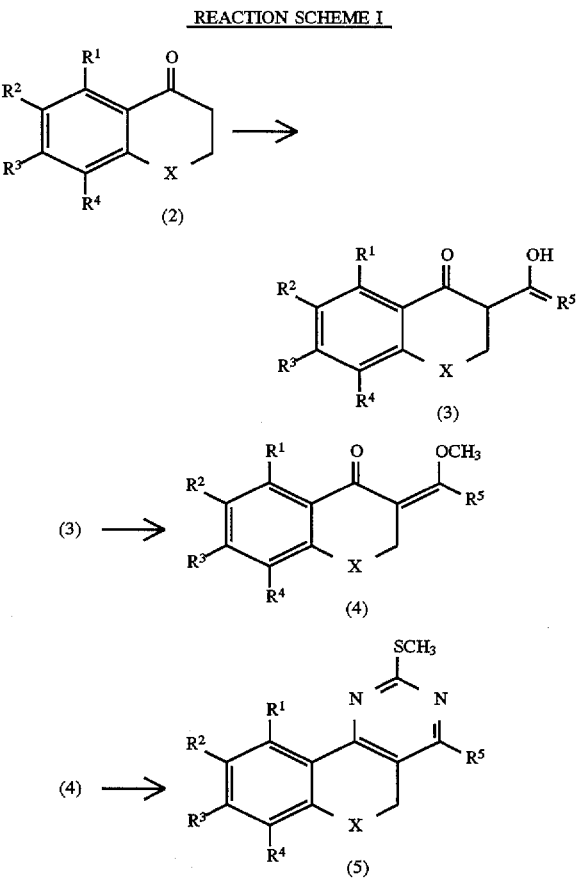

-continued
REACTION SCHEME I

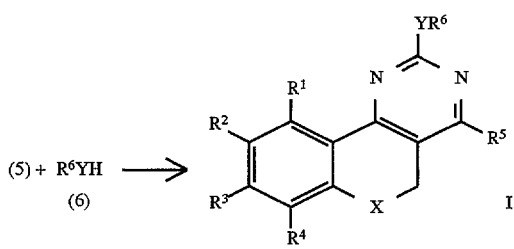

where $R^1$, $R^2$, $R^3$, $R^4$, $R^5$, $R^6$, X and Y are as defined in the Summary of the Invention.

Preparation of Compounds of Formula (3)

The starting 1-tetralone of formula (2) may be obtained commercially, for example from Aldrich Chemical Co., Inc., or may be prepared according to methods well known in the art. To prepare compounds of formula (3), a compound of formula (2) is treated with about 1 to 1.5 molar equivalents, preferably about 1.1 molar equivalents, of a non-nucleophilic base, for example lithium diisopropylamide, potassium t-butoxide, and the like. The reaction is preferably carried out in an ethereal solvent (for example diethyl ether, dimethoxyethane, dioxane or tetrahydrofuran, preferably a mixture of diethyl ether and tetrahydrofuran), at a temperature of about 0° C., for about 15 minutes. After the salt formation is essentially complete, an acylating agent, for example an ester of formula $R^5C(O)R$, where R is lower alkyl and $R^5$ is as defined above but is not halo, e.g. ethyl formate, methyl acetate, and the like, is then added, and the temperature is allowed to rise to about room temperature over a period of about 45 minutes. The product of formula (3), a 2-formyl-1-tetralone derivative, is isolated by conventional means, and preferably reacted in the next step with no further purification.

Preparation of Compounds of Formula (4)

The 2-formyl-1-tetralone derivative of formula (3) is converted to the corresponding 2-enol ether of formula (4) by reacting a compound of formula (3) with an alcohol, preferably methanol, in the presence of a catalytic amount of a strong acid, preferably concentrated sulfuric acid. The reaction is preferably carried out at a temperature of about the reflux temperature of the alcohol, for about 5 minutes to 2 hours, preferably about 15 minutes. The product of formula (4), a 2-methoxymethylene-1-tetralone derivative, is isolated by conventional means, preferably by precipitation and filtration, and is reacted in the next step without any further purification.

Preparation of Compounds of Formula (5)

The 2-methoxymethylene-1-tetralone derivative of formula (4) is reacted with 2-methyl-2-thiopseudourea to give the corresponding quinazoline derivative of formula (5). The reaction is preferably carried out in an ethereal solvent (for example diethyl ether, dimethoxyethane, dioxane or tetrahydrofuran, preferably tetrahydrofuran), at the reflux temperature of the solvent, preferably about 70° C., for about 5–30 hours, preferably about 16 hours. The product of formula (5), a 2-methylthio-5,6-dihydrobenzo[h]quinazoline derivative, is isolated by conventional means.

Preparation of Compounds of Formula I

The 2-methylthio-5,6-dihydrobenzo[h]quinazoline derivative of formula (5) is reacted with the anion of a compound of formula (6), in which $R^6$ and Y are as defined in the Summary of the Invention. The anion is preferably generated by reaction with a strong base, for example n-butyl lithium or sodium hydride. The reaction is preferably carried out in an ethereal solvent (for example diethyl ether, dimethoxyethane, dioxane or tetrahydrofuran, preferably tetrahydrofuran), at the reflux temperature of the solvent, preferably about 70° C., for about 1–10 hours, preferably about 4 hours. The product of Formula I, a 2-substituted-5,6-dihydrobenzo[h]quinazoline derivative, is isolated by conventional means. This compound may then be converted to an acid salt, preferably the hydrochloride.

Alternative Method of Conversion of (5) to Formula I

An alternative procedure for the preparation of compounds of Formula I from compounds of formula (5) is shown below in Reaction Scheme IA.

REACTION SCHEME IA

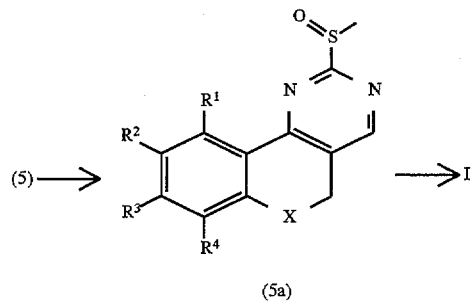

Preparation of Compounds of Formula (5a)

The 2-methylthio-5,6-dihydrobenzo[h]quinazoline derivative of formula (5) is reacted with an oxidizing agent, preferably m-chloroperbenzoic acid, in an inert solvent, preferably dichloromethane. The reaction is preferably carried out at a temperature of about −30° to −70° C., preferably about −50° C., for about 5 minutes to 5 hours, preferably about 30 minutes. The product of formula (5a), a 2-methylsulfoxide-5,6-dihydrobenzo[h]quinazoline derivative, is isolated by conventional means.

Preparation of Compounds of Formula I

The 2-methylsulfoxide-5,6-dihydrobenzo[h]quinazoline derivative of formula (5a) is then converted to a compound of Formula I by the method shown in Reaction Scheme I for the conversion of (5) to I.

Alternative Method of Preparation of Compounds of Formula I

An alternative method of preparing compounds of Formula I is shown below in Reaction Scheme II.

REACTION SCHEME II

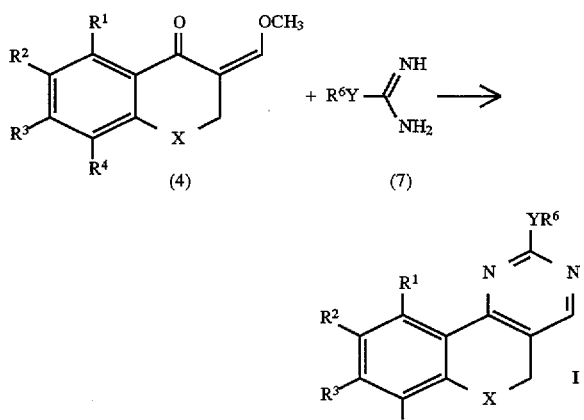

Preparation of Compounds of Formula I

The 2-methoxymethylene-1-tetralone derivative of formula (4), prepared as shown in Reaction Scheme I, is reacted with a compound of formula (7), in which $R^6$ and Y are as defined in the Summary of the Invention. Compounds of formula (7) are obtained commercially, for example from Aldrich, or may be prepared by the method shown in J. Org. Chem. (1992), Vol. 57, 2497, and "Organic Functional Group Preparation", Volume III, 2nd Ed., S. R. Sandler and W. Karo, Academic Press Inc. (1989). The reaction is preferably carried out in an ethereal solvent (for example diethyl ether, dimethoxyethane, dioxane or tetrahydrofuran, preferably tetrahydrofuran), at the reflux temperature of the solvent, preferably about 70° C., for about 1–10 hours, preferably about 4 hours. The product of Formula I, a 2-substituted-5,6-dihydrobenzo[h]quinazoline derivative, is isolated by conventional means. This compound may then be converted to an acid salt, preferably the hydrochloride.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of Formula I are basic, and thus may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of Formula I may be converted to the corresponding free bases by treatment with at least a stoichiometric amount of a suitable base such as sodium or potassium hydroxide, potassium carbonate, sodium bicarbonate, ammonia, and the like.

Preferred Processes

In summary, compounds of Formula I are prepared according to the following last steps:

1. A process for preparing compounds of Formula I comprises:

reacting a compound of the formula:

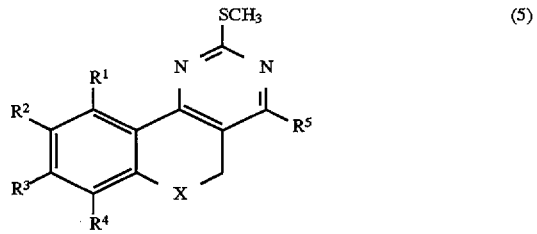

with an anion of a compound of formula $R^6YH$, where $R^6$ and Y are as defined in the Summary of the Invention.

2. Alternatively, a process for preparing compounds of Formula I comprises:

reacting a compound of the formula:

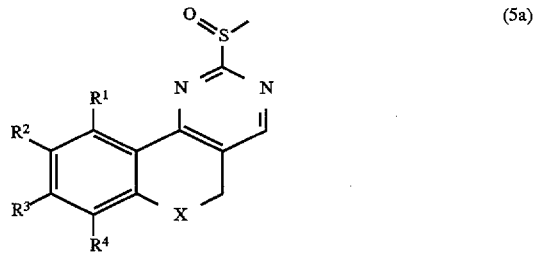

with an anion of a compound of formula $R^6YH$, where $R^6$ and Y are as defined in the Summary of the Invention.

3. Alternatively, a process for preparing compounds of Formula I comprises:

reacting a compound of the formula:

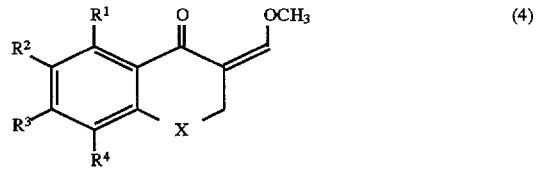

with a compound of formula (7), i.e. $R^6YC(NH)NH_2$, where $R^6$ and Y are as defined in the Summary of the Invention.

Utility and Administration

General Utility

The compounds of this invention are selective 5-$HT_{2C}$ receptor antagonists. Affinity for the 5-$HT_{2C}$ receptor was measured by a cloned rat 5-$HT_{2C}$ receptor binding assay (for details see Example 11, infra.). Antagonist properties were determined in NIH3T3 cells, transfected with cloned rat 5-HT$_{2C}$ receptor, by measuring the propensity of the compounds to inhibit 5-HT induced/5-HT$_{2C}$ mediated increases in cellular metabolic activity (for further details see Example 12, infra.). Accordingly, the compounds of this invention are useful for treating diseases which can be ameliorated by blockade of 5-HT$_{2C}$ receptors. For example, clinical and experimental evidence support a therapeutic role for 5-HT$_{2C}$ receptor antagonists in treating anxiety. The 5-HT$_{2C}$ receptor agonist 1-(3-chlorophenyl)piperazine (mCPP) when administered to human volunteers causes anxiety (see Charney et al. (1987), *Psychopharmacology*, 92, 14–24). MCPP also produces anxiogenic effects in rat, social interaction (SI) and elevated X-maze models of anxiety, which effects are blocked by non-selective 5-HT$_{2C/2A}$ receptor antagonists but not by selective 5-HT$_{2A}$ receptor antagonists (see Kennett et al. (1989), *Eur. J. Pharmacol.*, 164, 445–454 and Kennett (1993), supra.). In addition, non-selective 5-HT$_{2C/2A}$ receptor antagonists by themselves produce anxiolytic effects in the SI and Geller Seifter conflict tests, while selective 5-HT$_{2A}$ receptor antagonists do not share this property.

Furthermore, mCPP when administered to panic disorder patients or obsessive compulsive disorder patients increases levels of panic and/or anxiety (see Charney et al. (1987), supra., and Zohar et al. (1987), *Arch. Gen. Psychiat.*, 44, 946–951). Thus, current evidence support the application of selective 5-HT$_{2C}$ receptor antagonists for treating generalized anxiety disorder, panic disorder and obsessive compulsive disorder.

Anxiolytic activity can be determined experimentally by the art-recognized Crawley and Goodwin two-compartment exploratory model (e.g., see Kilfoil et al. (1989), *Neuropharmacology*, 28(9), 901–905). In brief, the method measures the extent a compound affects the natural anxiety of mice in a novel, brightly lighted area (for further details see Example 32, infra.).

Clinical and experimental evidence support a therapeutic role for selective 5-HT$_{2C}$ receptor antagonists in treating chemical dependency. The 5-HT$_{2C}$ receptor agonist mCPP induces a craving for alcohol in abstaining alcoholics (see Benkelfat et al. (1991), *Arch. Gen. Psychiat.*, 48, 383). In contrast, the non-selective 5-HT$_{2C/2A}$ receptor antagonist ritanserin reduces alcohol preference in rats (see Meert et al., (1991), *Drug Development Res.* 24, 235–249), while the selective 5-HT$_{2A}$ receptor antagonist ketanserin has no affect on preference for alcohol (see Kennett et al., (1992), *J. Psychopharmacol.*, Abstr. A26). Ritanserin also reduces both cocaine and fentanyl preference in rat models of addiction (see Meert et al. (1991), *Drug Development Res.* 25, 39–53 and Meert et al., (1991), *Drug Development Res.* 25, 55–66). Clinical studies show that ritanserin decreases alcohol intake in chronic alcoholics (see Monti et al. (1991), *Lancet.* 337, 60) and is useful in patients withdrawing from other drugs of abuse (see Sadzot et al. (1989), *Psychopharmacology*, 98, 495–499). Thus, current evidence support the application of selective 5-HT$_{2C}$ receptor antagonists for treating alcoholism and addiction to other drugs of abuse.

Ameliorating effects of compounds during withdrawal from drugs of abuse can be determined experimentally by the mouse, withdrawal anxiety test, an accepted assay (e.g., see Carboni et al. (1988), *Eur. J. Pharmacol*, 151, 159–160). This procedure utilizes the exploratory model described above to measure the extent a compound ameliorates the symptoms of withdrawal that occur after chronically treating with an addictive substance and then abruptly ceasing the treatments (for further details see Example 33, infra.).

Clinical evidence support a therapeutic role for selective 5-HT$_{2C}$ receptor antagonists in treating depression. For example, non-selective 5-HT$_{2C/2A}$ receptor antagonists show clinical efficacy in treating depression (see Murphy (1978), *Brit. J. Pharmacol.*, 5, 81S–85S; Klieser et al. (1988), *Pharmacopsychiat.*, 21, 391–393; and Camara (1991), *Biol. Psychiat.*, 29, 201A). Furthermore, experimental results suggest that the mechanism by which conventional antidepressant drugs exert their therapeutic efficacy is through adaptive changes in the serontinergic system (see Anderson (1983), *Life Sci*, 32, 1791–1801). For example, chronic treatment with monamine oxidase inhibitors reduce mCPP-induced/5-HT$_{2C}$ mediated functional responses in a variety of paradigms. Similar effects are exhibited by selective 5-HT reuptake inhibitors. These findings suggest that treatments which enhance extraneuronal 5-HT levels desensitize 5-HT$_{2C}$ receptor function which in turn causes, or contributes to, antidepressant activity (see Kennett (1993), supra.).

Clinical evidence support a therapeutic role for selective 5-HT$_{2C}$ receptor antagonists in treating migraine. The 5-HT$_{2C}$ receptor agonist mCPP when administered to human volunteers causes migraine-like headaches. In contrast, non-selective 5-HT$_{2C/2A}$ receptor antagonists are clinically effective antimigraine agents, while the selective 5-HT$_{2A}$ receptor antagonist ketanserin is not (see Winther (1985), *Cephalalgia*, 5, 402–403). Furthermore, experimental results suggest that the clinical efficacy of chronic administration of 5-HT reuptake inhibitors as migraine prophylactics is due to desensitization of 5-HT$_{2C}$ receptors (see Kennett (1993), supra., and the above discussion on 5-HT$_{2C}$ receptor desensitization and depression).

Clinical evidence support a therapeutic role for 5-HT$_{2C}$ receptor antagonists in treating sleep disorders. The 5-HT$_{2C}$ receptor agonist mCPP when administered to human volunteers reduces total sleep time, sleep efficiency, slow wave sleep (SWS) and rapid eye movement sleep (see Lawlor et al. (1991), *Biol. Psychiat.*, 29, 281–286). In contrast, the non-selective 5-HT$_{2C/2A}$ receptor antagonist ritanserin increases SWS, reduces sleep onset latency and improves subjective sleep quality in healthy volunteers (see Idzikowski et al. (1986), *Brain Res.*, 378, 164–168; Idzikowski et al. (1987), *Psychopharmacology*, 93, 416–420; Declerck et al. (1987), *Curr. Therap. Res.*, 41, 427–432; and Adam et al. (1989), *Psychopharmacology*, 99, 219–221). Thus, given the opposing effects of 5-HT$_{2C}$ receptor stimulation and 5-HT$_{2C}$ receptor antagonism, selective 5-HT$_{2C}$ receptor antagonists could be of particular therapeutic value in treating sleep disorder (see Kennett (1993), supra.).

Clinical evidence support a therapeutic role for 5-HT$_{2C}$ receptor antagonists in feeding disorders. Non-specific 5-HT$_{2C/2A}$ receptor antagonists are shown to produce increased appetite and weight gain. Thus, there is some clinical evidence to support the application of selective 5-HT$_{2C}$ receptor antagonists for the treatment of anorexia nervosa.

Experimental evidence support a therapeutic role for 5-HT$_{2C}$ receptor antagonists in treating priapism. MCPP produces penile erections in rats, which effect is blocked by non-selective 5-HT$_{2C/2A}$ receptor antagonists but not by selective 5-HT$_{2A}$ receptor antagonists (see Hoyer (1989), In: Fozard J. (ed.) *Peripheral actions of 5-HT*, Oxford University Press, Oxford, 72–99).

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dose for oral, parenteral and otherwise systemic routes of administration is in the range of 0.01–20 mg/kg/day, preferably 0.1–10 mg/kg/day. For an average 70 kg human, this would amount to 0.7–1400 mg per day, or preferably 7–700 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of Formula I or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%–95% active ingredient, more preferably 2–50%, most preferably 5–8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1% to 10%, most preferably 0.5% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.5% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Examples 4–10.

The following preparation and examples illustrate the invention but are not intended to limit its scope.

PREPARATION 1

Preparation of 3,5-dimethoxy-4-ethoxyaniline

A. Preparation of 1,3-dimethoxy-2-ethoxybenzene

To a stirred solution of 2,6-dimethoxyphenol (10 g) in dimethylsulfoxide (100 ml) under nitrogen was added a solution of sodium hydroxide (3.2 g) in water (20 ml). The mixture was warmed to 50° C., ethyl iodide (12.4 g) added, and stirring continued at 50° C. for 4 hours. The product was poured into 1 liter of water and the mixture extracted with diethyl ether. The extract was washed sequentially with 20% potassium hydroxide, water, and brine, and then dried over magnesium sulfate. Removal of the solvent under reduced pressure gave 1,3-dimethoxy-2-ethoxybenzene as a colorless oil (6.71 g).

B. Preparation of 3,5-dimethoxy-4-ethoxynitrobenzene

The oil obtained in A was dissolved in acetic acid (15 ml) at room temperature, stirred, and 70% nitric acid (4.1 ml) added dropwise, maintaining the temperature between 30°–50 C. After 30 minutes the mixture was poured into water, and the precipitated solid filtered off. The solid was recrystallized from ethanol, to give 3,5-dimethoxy-4-ethoxynitrobenzene (3.5 g). A further 2.8 g was obtained from the filtrate.

C. Preparation of 3,5-dimethoxy-4-ethoxyaniline

The product from B (1.2 g) was dissolved in absolute ethanol (50 ml), 10% palladium/carbon catalyst added, and the mixture stirred under hydrogen at room temperature for 8 hours. The catalyst was filtered off, and solvent removed from the filtrate under reduced pressure, to give 3,5-dimethoxy-4-ethoxyaniline (1.02 g), m.p. 88°–89° C.

PREPARATION 2

Preparation of N-Methyl-3,4,5-trimethoxyaniline

A. Preparation of Ethyl 3,4,5-trimethoxyphenylcarbamate

To a solution of 3,4,5-trimethoxyaniline (6 g) in tetrahydrofuran (125 ml) at room temperature was added potassium carbonate (5.42 g) followed by ethyl chloroformate (3.55 g). The mixture was stirred at room temperature for 48 hours, then solvent removed under reduced pressure. The residue was stirred with diethyl ether and filtered. The solid material remaining on the filter was extracted with acetone, the organic extracts combined, and solvent removed from the combined extracts under reduced pressure, to give a residue of ethyl 3,4,5-trimethoxyphenylcarbamate (6.05 g)

B. Preparation of N-Methyl-3,4,5-trimethoxyaniline

To a solution of ethyl 3,4,5-trimethoxyphenylcarbamate (6.0 g) in tetrahydrofuran (150 ml) was added a 1M solution of lithium aluminum hydride in tetrahydrofuran (23.5 ml) dropwise. The mixture was stirred at room temperature for 1 hour, then refluxed for 1 hour. The product was cooled and an excess of 1M sodium hydroxide added dropwise. The precipitate was filtered off, and the filtrate partitioned between ethyl acetate and water. The organic layer was dried over magnesium sulfate, and solvent removed under reduced pressure. The residue was redissolved in ethyl acetate and washed with 2M hydrochloric acid. The aqueous layer was washed with ethyl acetate, then basified with 1M sodium hydroxide, and extracted with ethyl acetate. The organic layer was dried over magnesium sulfate, and solvent removed under reduced pressure, to give N-methyl-3,4,5-trimethoxyaniline.

PREPARATION 3

Preparation of a Compound of Formula (3)

A. Preparation of (3) where $R^1$, $R^2$, $R^3$ are Hydrogen and $R^4$ is Methoxy To a solution of 5-methoxy-1-tetralone (10 g) in diethyl ether (100 ml) at 0° C. was added 1M potassium t-butoxide in tetrahydrofuran (68 ml) with stirring. After 15 minutes, ethyl formate (25 g) was added in one portion, and the reaction mixture allowed to rise to room temperature over a period of 45 minutes. The mixture was poured into water (500 ml), extracted with diethyl ether, the ether extract dried over magnesium sulfate, and solvent removed under reduced pressure to give 2-formyl-5-methoxy-1-tetralone (10.2 g), m.p. 67°–68° C.

B. Preparation of (3) varying $R^1$, $R^2$, $R^3$ and $R^4$

Similarly, replacing 5-methoxy-1-tetralone with:

1-tetralone;

6-methoxy-1-tetralone;

6-chloro-1-tetralone;

7-methoxy-1-tetralone;

and following the procedures of Preparation 3A above, the following compounds of formula (3) were prepared:

2-formyl-1-tetralone;

2-formyl-6-methoxy-1-tetralone;

2-formyl-6-chloro-1-tetralone; and 2-formyl-7-methoxy-1-tetralone.

C. Preparation of (3) varying $R^1$, $R^2$, $R^3$ and $R^4$

Similarly, replacing 5-methoxy-1-tetralone with other compounds of Formula (2) and following the procedures of Preparation 3A above, other exemplary compounds of formula (3) are prepared.

PREPARATION 4

Preparation of a Compound of Formula (4)

A. Preparation of (4) where $R^1$, $R^2$, $R^3$ are Hydrogen and $R^4$ is Methoxy To a solution of 2-formyl-5-methoxy-1-tetralone (10.1 g) in anhydrous methanol (100 ml) was added three drops of concentrated sulfuric acid, and the mixture was refluxed for 15 minutes. The solution was poured into 500 ml of icewater, the resulting solid filtered off, washed with water, and dried under vacuum, to yield a tan solid (9.78 g). A $^1H$ NMR spectrum of this product showed the desired product 5-methoxy-2-methoxymethylene-1-tetralone, contaminated with about 10% of the corresponding acetal derivative; the mixture was used in the next reaction with no further purification.

B. Preparation of (4) varying $R^1$, $R^2$, $R^3$ and R4

Similarly, replacing 2-formyl-5-methoxytetralone with other compounds of formula (3) and following the procedures of Preparation 4A above, the following compound of formula (4) was prepared:

6-methoxy-2-methoxymethylene-1-tetralone.

C. Preparation of (4) varying $R^1$, $R^2$, $R^3$ and $R^4$

Similarly, replacing 2-formyl-5-methoxytetralone with other compounds of formula (3) and following the procedures of Preparation 4A above, other exemplary compounds of formula (4) are prepared, for example:

2-methoxymethylene-1-tetralone;

6-chloro-2-methoxymethylene-1-tetralone; and 7-methoxy-2-methoxymethylene-1-tetralone.

PREPARATION 5

Preparation of a Compound of Formula (5)

A. Preparation of (5) where $R^1$, $R^2$, $R^3$ are Hydrogen, $R^4$ is Methoxy, and X is $CH_2$ To a solution of 5-methoxy-2-methoxymethylene-1-tetralone (9.78 g) in tetrahydrofuran (200 ml) was added 2-methyl-2-thiopseudourea sulfate (8.34 g), followed by potassium carbonate (9.7 g), and the mixture was refluxed overnight. Solvent was then removed under reduced pressure, the residue stirred with diethyl ether, and filtered. Concentration of the filtrate gave a brown solid, which upon crystallization from ethanol gave 7-methoxy-2-methylthio-5,6-dihydrobenzo[h]quinazoline (8.3 g) as a light brown solid.

A small portion (1.016 g) of this solid was dissolved in hot ethanol (50 ml) in the presence of decolorizing charcoal, filtered, and water was added to the hot filtrate until the solution became cloudy. Cooling to 0° C. gave a white crystalline solid, which was filtered off and dried under vacuum, m.p. 106.1°–106.8° C.

B. Preparation of (5) varying $R^1$, $R^2$, $R^3$ and $R^4$

Similarly, replacing 5-methoxy-2-methoxymethylene-1-tetralone with other compounds of formula (4) and following the procedures of Preparation 5A above, the following compound of formula (5) was prepared:

8-methoxy-2-methylthio-5,6-dihydrobenzo[h] quinazoline;

C. Preparation of (5) varying $R^1$, $R^2$, $R^3$ and $R^4$

Similarly, replacing 5-methoxy-2-methoxymethylene-1-tetralone with other compounds of formula (4) and following the procedures of Preparation 5A above, other exemplary compounds of formula (5) are prepared, for example:

2-methylthio-1-tetralone;

8-chloro-2-methylthio-1-tetralone; and 9-methoxy-2-methylthio-1-tetralone.

PREPARATION 6

Preparation of a Compound of Formula (5a)

A. Preparation of (5a) where $R^1$, $R^2$, $R^4$ are Hydrogen, $R^3$ is Methoxy, and X is $CH_2$ To a solution of 8-methoxy-2-methylthio-5,6-dihydrobenzo[h]quinazoline (300 mg) in methylene chloride (25 ml) cooled to −50° C. was added m-chloroperbenzoic acid (400 mg). The mixture was stirred at −50° C. for 30 minutes, then at −30° C. for 30 minutes, and extracted with aqueous 1M sodium hydroxide solution. The organic layer was dried over magnesium sulfate, and solvent removed under reduced pressure to give 8-methoxy-2-methylsulfoxide-5,6-dihydrobenzo[h]-quinazoline.

EXAMPLE 1

Preparation of a Compound of Formula I

A. Preparation of I where $R^1$, $R^2$, $R^3$, $R^5$ are Hydrogen, $R^4$ is Methoxy, $R^6$ is 3,4,5-trimethoxyohenyl, X is $CH_2$, and Y is NH To a solution of 3,4,5-trimethoxyaniline (0.401 g) in tetrahydrofuran at room temperature under nitrogen was added sodium hydride (60% oil dispersion, 0.16 g) in portions over 2–3 minutes. The mixture was stirred for 15 minutes, and then 7-methoxy-2-methylthio-5,6-dihydrobenzo[h]quinazoline (0.258 g) was added, and the mixture was refluxed for 4 hours. The reaction mixture was poured into 300 ml of water, and the resulting yellow precipitate filtered off, washed with pentane, and dried under vacuum, giving 7-methoxy-2-(3,4,5-trimethoxyanilino)-5,6-dihydrobenzo[h]quinazoline (0.3042 g).

Preparation of Hydrochloride Salt

This product (0.271 g) was slurried in hot ethanol (15 ml) and 1 ml of 3M hydrochloric acid in ethanol was added. An orange solution resulted, from which orange crystals rapidly formed. The mixture was cooled to 0° C., filtered, and the solid washed with ether, to give 7-methoxy-2-(3,4,5-trimethoxyanilino)-5,6-dihydrobenzo[h]quinazoline hydrochloride (0.265 g) as an orange solid, m.p. 228°–229.5° C.

B. Preparation of I varying $R^1$, $R^2$, $R^3$, $R^4$, $R^5$, and $R^6$

Similarly, replacing 3,4,5-trimethoxyaniline with 3,4,5-triethoxyaniline or 4-ethoxy-3,5-dimethoxyaniline and following the procedures of Example 1A above, the following compounds of Formula I were prepared:

7-methoxy-2-(3,4,5-triethoxyanilino)-5,6-dihydrobenzo[h]quinazoline, m.p 178.3–178.7;

7-methoxy-2-(3,4,5-triethoxyanilino)-5,6-dihydrobenzo[h]quinazoline hydrochloride, m.p. 233.7–234.6;

7-methoxy-2-(3,5-dimethoxy-4-ethoxyanilino)-5,6-dihydrobenzo[h]quinazoline;

7-methoxy-2-(3,5-dimethoxy-4-ethoxyanilino)-5,6-dihydrobenzo[h]quinazoline hydrochloride, m.p. 246–246.5;

8-methoxy-2-(4-methoxyanilino)-5,6-dihydrobenzo[h]-quinazoline hydrochloride, m.p. 212.8°–213.7° C.;

8-methoxy-2-(3,4,5-trimethoxyanilino)-5,6-dihydrobenzo[h]quinazoline hydrochloride, m.p. 213°–214° C.;

8-methoxy-2-(3,5-dimethoxyanilino)-5,6-dihydrobenzo[h]quinazoline hydrochloride, m.p. 220°–221° C.;

8-methoxy-2-(3,4-methylenedioxyanilino)-5,6-dihydrobenzo[h]quinazoline hydrochloride, m.p. 237°–238° C.;

8-methoxy-2-(3,4-dimethoxyanilino)-5,6-dihydrobenzo[h]quinazoline hydrochloride, m.p. 215°–217° C.;

8-methoxy-2-(2,4-dimethoxyanilino)-5,6-dihydrobenzo[h]quinazoline hydrochloride, m.p. 230°–231° C.; and 8-methoxy-2-[N-(3,4,5-trimethoxyphenyl-N-methylamino)-5,6-dihydrobenzo[h]quinazoline hydrochloride, m.p. 199°–210° C.

C. Preparation of I varying $R^1$, $R^2$, $R^3$, $R^4$, $R^5$, $R^6$, X and Y

Similarly, optionally replacing 3,4,5-trimethoxyaniline with other compounds of formula (6), and optionally replacing 7-methoxy-2-methylthio-5,6-dihydrobenzo[h] quinazoline with other compounds of formula (5), and following the procedures of Example 1A above, the following compounds of Formula I were prepared:

8-methoxy-10H-9-oxa-3-(3,4,5-trimethoxyanilino)-2,4-diazaphenanthrene hydrochloride, m.p. 225.5°–226.8° C.; and 7-methoxy-2-[(1-methyl-1H-indol-5-yl)amino]-5,6-dihydrobenzo[h]quinazoline hydrochloride, m.p. 250°–251.5° C.

EXAMPLE 2

Alternative Preparation of a Compound of Formula I

A. Preparation of I where $R^1$, $R^2$, $R^4$, $R^5$ are Hydrogen, $R^3$ is Methoxy, $R^6$ is 4-methoxyphenyl, X is $CH_2$, and n is O To a solution of 4-methoxyphenylamidine hydrochloride ((201 mg) in ethanol (4 ml) was added sodium methoxide (79 mg), followed by a solution of 6-methoxy-2-methoxymethylene-1-tetralone (200 mg) in ethanol (2 ml). The mixture was refluxed for 2.5 hours, then stirred at room temperature overnight. The mixture was then poured into diethyl ether, extracted with water, dried over magnesium sulfate, and solvent removed. The residue was dissolved in ethanol/hydrochloric acid, from which crystals were obtained. A small portion of ether was added, and the crystals filtered off and dried under vacuum, yielding 8-methoxy-2-(4-methoxyphenyl)-5,6-dihydrobenzo[h]quinazoline hydrochloride (0.265 g), m.p. 198°–205° C.

B. Preparation of I varying $R^1$, $R^2$, $R^3$, $R^4$, $R^5$, and $R^6$

Similarly, optionally replacing 4-methoxyphenylamidine hydrochloride with other compounds of formula (7), and optionally replacing 6-methoxy-2-methoxymethylene-1-tetralone with other compounds of formula (4) and following the procedures of Example 2A above, the following compounds of Formula I were prepared:

8-methoxy-2-(4-pyridyl)-5,6-dihydrobenzo[h]quinazoline hydrochloride, m.p. 243.6–244.1.

C. Preparation of I varying $R^1$, $R^2$, $R^3$, $R^4$, $R^5$, and $R^6$

Similarly, optionally replacing 4-methoxyphenylamidine hydrochloride with other compounds of formula (7), and optionally replacing 6-methoxy-2-methoxymethylene-1-tetralone with other compounds of formula (4) and following the procedures of Example 2A above, other compounds of Formula I are prepared.

EXAMPLE 3

Alternative Preparation of a Compound of Formula I

A. Preparation of I where $R^1$, $R^2$, $R^4$, $R^5$ are Hydrogen, $R^3$ is Methoxy, $R^6$ is 3,4,5-trimethoxyphenyl, X is $CH_2$ and Y is $NR^7$ in which $R^7$ is Methyl To a solution of N-methyl-3,4,5-trimethoxyaniline (255 mg) in tetrahydrofuran (25 ml) at 0° C. under nitrogen was added n-butyl lithium (0.517 ml of 2.5M in hexane), and the mixture stirred for 15 minutes. To this mixture was added a solution of 8-methoxy-2-methylsulfoxide-5,6-dihydrobenzo[h]quinazoline (313 mg) in tetrahydrofuran (5 ml), and the stirring continued for a further 15 minutes at 0° C., followed by refluxing for 3 hours. Solvent was removed under reduced pressure, the residue stirred with diethyl ether, filtered, and solvent removed from the filtrate. The residue was dissolved in methylene chloride, washed with 1M sodium hydroxide, dried over magnesium sulfate, and solvent removed under reduced pressure. The residue was converted into the hydrochloride salt in ethanol/hydrochloric acid mixture, the precipitate filtered off and recrystallized from a mixture of ethanol/cyclohexane/diethyl ether (1:5:15), to give 8-methoxy-2-(N-methyl-3,4,5-trimethoxyanilino)-5,6-dihydrobenzo[h]quinazoline, m.p. 199°–201° C.

EXAMPLE 4

This example illustrates the preparation of a representative pharmaceutical formulation for oral administration containing an active compound of Formula I, e.g. 7-methoxy-2-(3,4,5-trimethoxyanilino)-5,6-dihydrobenzo[h]quinazoline.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I, such as those prepared in accordance with Examples 1–3, can be used as the active compound in the preparation of the orally administrable formulations of this example.

EXAMPLE 5

This example illustrates the preparation of another representative pharmaceutical formulation for oral administration containing an active compound of Formula I, e.g., 7-methoxy-2-(3,4,5-trimethoxyanilino)-5,6-dihydrobenzo[h]quinazoline.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I, such as those prepared in accordance with Examples 1–3, can be used as the active compound in the preparation of the orally administrable formulations of this example.

EXAMPLE 6

This example illustrates the preparation of a representative pharmaceutical formulation containing an active compound of Formula I, e.g.,7-methoxy-2-(3,4,5-trimethoxyanilino)-5,6-dihydrobenzo[h]quinazoline.

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I, such as those prepared in accordance with Examples 1–3, can be used as the active compound in the preparation of the orally administrable formulations of this example.

EXAMPLE 7

This example illustrates the preparation of a representative pharmaceutical formulation for oral administration containing an active compound of Formula I, e.g. 7-methoxy-2-(3,4,5-trimethoxyanilino)-5,6-dihydrobenzo[h]quinazoline.

An injectable preparation buffered to a pH of 4 is prepared having the following composition:

| Ingredients | |
|---|---|
| Active Compound | 0.2 g |
| Sodium Acetate Buffer Solution (0.4M) | 2.0 ml |
| HCL (1N) | q.s. to pH 4 |
| Water (distilled, sterile) | q.s. to 20 ml |

Other compounds of Formula I, such as those prepared in accordance with Examples 1–3, can be used as the active compound in the preparation of the injectable formulations of this example.

EXAMPLE 9

This example illustrates the preparation of a representative pharmaceutical formulation for topical application containing an active compound of Formula I, e.g., 7-methoxy-2-(3,4,5-trimethoxyanilino)-5,6-dihydrobenzo[h]quinazoline.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Examples 1–3, can be used as the active compound in the preparation of the topical formulations of this example.

EXAMPLE 10

This example illustrates the preparation of a representative pharmaceutical formulation containing an active compound of Formula I, e.g., 7-methoxy-2-(3,4,5-trimethoxyanilino)-5,6-dihydrobenzo[h]quinazoline.

A suppository totalling 2.5 grams is prepared having the following composition:

| Ingredients | |
|---|---|
| Active Compound | 500 mg |
| Witepsol H-15* | balance |

(*triglycerides of saturated vegetable fatty acid; a product of Riches-Nelson, Inc., New York, N.Y.)

Other compounds of Formula I, such as those prepared in accordance with Examples 1–3, can be used as the active compound in the preparation of the suppository formulations of this example.

EXAMPLE 11

Cloned Rat $5\text{-HT}_{2C}$ Receptor Binding Assay

The following describes an in vitro binding assay utilizing cloned $5\text{-HT}_{2C}$ receptors radiolabelled with [$^3$H] mesulergine.

Mouse NIH3T3 fibroblasts expressing cloned $5\text{-HT}_{2C}$ receptor were maintained in Dulbecco's Modified Eagle medium with 10% Fetal Calf Serum and 250 µg/mL G418 in 95/5% $O_2/CO_2$. The cells were harvested using 2 mM EDTA in phosphate buffered saline (calcium/magnesium free) and centrifuged (500 g). The cell pellet was homogenized using a Polytron P10 disrupter (setting 5, 5 sec) in homogenization buffer (Tris, 50 mM; $Na_2EDTA$, 5 mM) and the homogenate was centrifuged at 19,500 rpm using a Sorvall/Dupont RC5C centrifuge with an SS34 rotor (30,000–48,000 g, 15 minutes). The pellet was homogenized (setting 5, 5 sec) in homogenization buffer and the homogenate was centrifuged (30,000–48,000 g, 15 minutes). The pellet was homogenized (setting 5, 5 sec) in resuspension buffer (Tris, 50 mM; EDTA 0.5 mM) and the homogenate was centrifuged (30,000–48,000 g, 15 minutes). The pellet was homogenized (setting 5, 5 sec) in a small volume of resuspension buffer to give approximately $1\times10^7$ cells/mL. The membranes were separated into 1 mL aliquots and stored at $-70°$ C.

The membranes were thawed at room temperature and diluted with assay buffer (NaCl, 118 mM; KCl, 4.5 mM; $KH_2PO_4$, 1.2 mM; $CaCl_2.2H_2O$, 2.5 mM; $MgCl_2$, 1 mM; D-glucose, 10 mM; Tris, 25 mM). An optimal dilution ratio was predetermined for each batch of membranes to ensure that less than 10% of $5\times10^{-10}$M [$^3$H]mesulergine binds, specific binding is at least 10 times greater than a machine background of 23 dpm and the best ratio of specific binding to total binding is achieved. The membranes were homogenized (setting 5, 5 sec) and then the homogenated was added to assay tubes containing mesulergine ($5\times10^{-10}$M), test compound ($1\times10^{-10}$–$1\times10^{-4}$M) and assay buffer (q.s. to 500 µL). The assay mixture was incubated at 32° C. for 60 minutes and then filtered over 0.1% polyethyleneimine pretreated glass fiber filtermats using a Brandel cell harvester. The assay tubes were rinsed with cold 0.1M sodium chloride (3×3 sec) and dried by drawing air over the filter for 10 seconds. Radioactivity retained on the filters was determined by liquid scintillation counting. In a similar fashion, total binding was measured with methysergide ($1\times10^{-5}$M) in the absence of test compound. For each compound tested the concentration producing 50% inhibition of binding ($IC_{50}$) was determined using iterative curve fitting techniques.

Proceeding as in Example 11, compounds of the invention were found to have affinity for the $5\text{-HT}_{2C}$ receptor.

EXAMPLE 12

Cloned Rat $5\text{-HT}_{2C}$ Receptor Functional Assay

The following describes an in vitro functional assay utilizing 5-HT induced, $5\text{-HT}_{2C}$ mediated increases in NIH3T3 cellular metabolic activity.

Mouse NIH3T3 fibroblasts expressing cloned $5\text{-HT}_{2C}$ receptor were maintained in high glucose Dulbecco's Minimal Essential Medium (DMEM) further comprising glutamine, sodium pyruvate and 10% Fetal Bovine. The cells were harvested using 2 mM EDTA in phosphate buffered saline and transferred to 6.5 mm transwell capsule plates (3 micron pore size) to give approximately $1\times10^5$ cells/capsule. The cells were allowed to adhere overnight and then transwell spacers and inserts were added to each transwell capsule. The capsules were placed into sensor chambers and the sensor chambers were loaded onto a microphysiometer. The $5\text{-HT}_{2C}$ receptor antagonist properties of test compounds were appraised by determining their affect on 5-HT induced increases in cellular metabolic activity, expressed as percent increase in acidification rate. Microphysiometer Running Medium (high glucose, sodium bicarbonate free DMEM) was pumped through the transwell capules for 1.5 minutes, 30 seconds of which 5-HT was present in the medium, followed by a 45 minute washout and recovery period. In this manner, cells were exposed to 5-HT in a non-cumulative concentration fashion, increasing in concentration until maximal or near maximal effect was observed.

Concentration-effect curves were constructed for 5-HT with and without the test compound present. Data was analyzed by iterative curve fitting techniques and the concentration ratio (CR) of 5-HT necessary to produce equiactive responses in the absence and presence of the test compound was determined. Relying on the concentration ratio, the molar concentration of the test compound, and the relationship:

$$pK_b = -\log \frac{[\text{test compound}]}{CR - 1}$$

the negative log of the dissociation constant ($pK_b$) for each test compound was determined.

The compounds of the present invention are found to be antagonists at the 5-HT$_{2C}$ receptor when tested by this method.

EXAMPLE 13

ANXIOLYTIC BEHAVIOR ASSAY

The following describes an in vivo method for determining anxiolytic activity by measuring the extent the drug affects the natural anxiety of mice when exposed to a novel, brightly lighted environment.

Naive male C5Bl/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is reflected by increased latency (the time for the mouse to move to the dark chamber when first placed in the center of the lighted area), increase in shuttle activity, increased or unaltered locomotor activity (number of grid lines crossed) and decreased time spent in the dark compartment.

The compounds of the present invention show amelioration of anxiolytic behavior when tested by this method.

EXAMPLE 14

WITHDRAWAL ANXIETY ASSAY

The following describes an in vivo procedure for determining amelioration of the symptoms caused by withdrawal from addictive substances by measuring the extent the drug affects the anxiety that occurs in mice after chronically treating with an addictive substance and then abruptly ceasing the treatments.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 14). Anxiolysis is seen as a general increase in exploratory activity in the lighted area. An increase in exploratory activity is reflected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0% w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the ethanol, cocaine or nicotine treatment is ceased.

The compounds of the present invention show amelioration of the symptoms caused by withdrawal from addictive substances when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

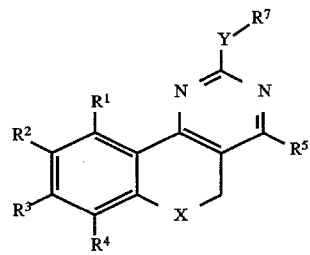

wherein:
$R^1$, $R^2$, $R^3$, $R^4$, and $R^5$ are independently hydrogen, lower alkyl, lower alkoxy, halo, or trifluoromethyl;

X is oxygen, sulfur, $N^7$, or $CH_2$;

Y is $NR^7$;

in which $R^7$ is hydrogen or lower alkyl; and $R^6$ is optionally substituted aryl;

and the pharmaceutically acceptable acid addition salts thereof.

2. The compound of claim 1, wherein X is $CH_2$, or a pharmaceutically acceptable salt thereof.

3. The compound of claim 2, wherein $R^5$ is hydrogen or a pharmaceutically acceptable salt thereof.

4. The compound of claim 3, wherein $R^1$, $R^2$, $R^3$, and $R^4$ are independently hydrogen or lower alkoxy, or a pharmaceutically acceptable salt thereof.

5. The compound of claim 4, wherein $R^1$, $R^2$, and $R^3$ are hydrogen, and $R^4$ is lower alkoxy, or a pharmaceutically acceptable salt thereof.

6. The compound of claim 5, wherein $R^6$ is phenyl optionally mono, di, or trisubstituted by lower alkoxy, or a pharmaceutically acceptable salt thereof.

7. The compound of claim 6, wherein $R^4$ is methoxy and $R^6$ is 3,4,5-trimethoxyphenyl, namely 7-methoxy-2-(3,4,5-trimethoxyanilino)-5,6-dihydrobenzo[h]quinazoline, or a pharmaceutically acceptable salt thereof.

8. The compound of claim 6, wherein $R^4$ is methoxy and $R^6$ is 3,4,5-triethoxyphenyl, namely 7-methoxy-2-(3,4,5-triethoxyanilino)-5,6-dihydrobenzo[h]quinazoline, or a pharmaceutically acceptable salt thereof.

9. The compound of claim 6, wherein $R^4$ is methoxy and $R^6$ is 3,5-dimethoxy-4-ethoxyphenyl, namely 7-methoxy-2-(3,5-dimethoxy-4-ethoxyanilino)-5,6-dihydrobenzo[h]quinazoline, or a pharmaceutically acceptable salt thereof.

10. The compound of claim 5, wherein $R^6$ is indole optionally mono, di, or trisubstituted by lower alkyl, or a pharmaceutically acceptable salt thereof.

11. The compound of claim 10, wherein $R^6$ is 1-methyl-1H-indol-5-yl, namely 7-methoxy-2-[(1-methyl-1H-indol-5-yl)amino]-5,6-dihydrobenzo[h]quinazoline, or a pharmaceutically acceptable salt thereof.

12. A pharmaceutical composition comprising a therapeutically effective amount of a compound of claim 1, or a pharmaceutically acceptable salt thereof, in admixture with one or more pharmaceutically acceptable non-toxic carriers.

13. A method for treating a mammal having a disease state which is alleviable by treatment with a $5HT_{2C}$ antagonist, which comprises administering to a mammal in need thereof a therapeutically effective amount of a compound of claim 1, or a pharmaceutically acceptable salt thereof.

14. The method of claim 13, wherein the disease state is selected from the group consisting of generalized anxiety disorder, panic disorder, obsessive compulsive disorder, alcoholism, depression, migraine, sleep disorders, anorexia nervosa, and priapism.

15. The method of claim 14, wherein the disease state is migraine.

16. A pharmaceutical composition comprising a therapeutically effective amount of a compound of claim 2, or a pharmaceutically acceptable salt thereof, in admixture with one or more pharmaceutically acceptable non-toxic carriers.

17. A method for treating a mammal having a disease state which is alleviable by treatment with a $5HT_{2C}$ antagonist, which comprises administering to a mammal in need thereof a therapeutically effective amount of a compound of claim 2, or a pharmaceutically acceptable salt thereof.

18. The method of claim 17, wherein the disease state is selected from the group consisting of generalized anxiety disorder, panic disorder, obsessive compulsive disorder, alcoholism, depression, migraine, sleep disorders, anorexia nervosa, and priapism.

19. The method of claim 18, wherein the disease state is migraine.

* * * * *